(12) United States Patent
Camacho et al.

(10) Patent No.: US 11,549,088 B2
(45) Date of Patent: Jan. 10, 2023

(54) APPARATUS AND METHOD FOR SYNGAS BIO-METHANATION

(71) Applicant: SUEZ GROUPE, Paris la Défense (FR)

(72) Inventors: Patricia Camacho, Croissy sur Seine (FR); Mathieu Haddad, Rueil Malmaison (FR)

(73) Assignee: SUEZ INTERNATIONAL, Paris (FR)

( * ) Notice: Subject to any disclaimer, the term of this patent is extended or adjusted under 35 U.S.C. 154(b) by 93 days.

(21) Appl. No.: 16/624,264

(22) PCT Filed: Jun. 7, 2018

(86) PCT No.: PCT/EP2018/065061
§ 371 (c)(1),
(2) Date: Dec. 18, 2019

(87) PCT Pub. No.: WO2018/234058
PCT Pub. Date: Dec. 27, 2018

(65) Prior Publication Data
US 2020/0115664 A1    Apr. 16, 2020

(30) Foreign Application Priority Data
Jun. 23, 2017   (EP) ..................................... 17305780

(51) Int. Cl.
*C12M 3/00*       (2006.01)
*C12P 5/00*       (2006.01)
(Continued)

(52) U.S. Cl.
CPC ............ *C12M 21/04* (2013.01); *C02F 11/04* (2013.01); *C12M 23/24* (2013.01); *C12M 25/12* (2013.01);
(Continued)

(58) Field of Classification Search
CPC ................................ C02F 11/04; C12M 21/04
See application file for complete search history.

(56) References Cited

U.S. PATENT DOCUMENTS 4,503,154 A * 3/1985 Paton ...................... C02F 3/286
                                                      210/603
7,431,833 B1 * 10/2008 Emmerich .............. B01F 33/81
                                                      210/220
(Continued)

FOREIGN PATENT DOCUMENTS

KR      10-0827351 B1    5/2008
WO      2013/110186 A1   8/2013
(Continued)

OTHER PUBLICATIONS

Luo, et al., "Anaerobic Digestion for Simultaneous Sewage Sludge Treatment and CO Biomethanation: Process Performance and Microbial Ecology", Environ. Sci. Technology, Sep. 4, 2013.
Zhang, et al., "Fatty acids production from hydrogen and carbon dioxide by mixed culture in the membrane biofilm reactor", Water Research, vol. 47, No. 16, pp. 6122-6129, Jul. 31, 2013.
(Continued)

*Primary Examiner* — Nathan A Bowers
(74) *Attorney, Agent, or Firm* — BakerHostetler

(57) ABSTRACT

A waste treatment, pyrolysis and gasification and concerns an apparatus for syngas bio-methanation include a unit for pyrolysis/gasification receiving organic material, the unit for pyrolysis/gasification generating syngas, comprising at least one membrane reactor inside a liquid bath comprising at least one bacteria population, the membrane reactor comprising at least one hollow fiber in contact with the liquid bath, around which a biofilm is formed and into which the syngas from the unit for pyrolysis/gasification flows, so as to convert the syngas into methane. A method for bio-methanation of syngas comprising a step of providing syngas from
(Continued)

a unit for pyrolysis/gasification to a membrane reactor inside a liquid bath comprising at least one suitable bacteria population, the membrane reactor comprising at least one hollow fiber in contact with the liquid bath, around which a biofilm is formed and into which the output syngas of the unit for pyrolysis flows, so as to convert the syngas into methane.

14 Claims, 8 Drawing Sheets

(51) Int. Cl.
- *C12M 1/107* (2006.01)
- *C02F 11/04* (2006.01)
- *C12M 1/04* (2006.01)
- *C12M 1/12* (2006.01)
- *C12M 1/00* (2006.01)
- *C12P 5/02* (2006.01)

(52) U.S. Cl.
CPC .......... *C12M 29/04* (2013.01); *C12M 29/16* (2013.01); *C12P 5/023* (2013.01)

(56) References Cited

U.S. PATENT DOCUMENTS

| | | | |
|---|---|---|---|
| 2012/0156744 A1* | 6/2012 | Macdonald | C12M 23/58 435/155 |
| 2014/0134686 A1* | 5/2014 | Schultz | C12P 7/065 435/140 |
| 2016/0153008 A1* | 6/2016 | Josse | C02F 11/10 435/167 |

FOREIGN PATENT DOCUMENTS

| | | |
|---|---|---|
| WO | 2014/165457 A1 | 10/2014 |
| WO | 2015/138627 A1 | 9/2015 |

OTHER PUBLICATIONS

Zhao, et al., "Performance of a Carboxydothermus hydrogenoformans-immobilizing membrane reactor for syngas upgrading into hydrogen", International Journal of Hydrogen Energy, vol. 38, Issue 5, pp. 2167-2175, Dec. 24, 2012.

* cited by examiner

APPARATUS AND METHOD FOR SYNGAS BIO-METHANATION

CROSS-REFERENCE TO RELATED APPLICATIONS

This application is a National Stage of International patent application PCT/EP2018/065061, filed on Jun. 7, 2018, which claims priority to foreign European patent application No. EP 17305780.3, filed on Jun. 23, 2017, the disclosures of which are incorporated by reference in their entirety.

TECHNICAL FIELD OF THE INVENTION

The invention relates to the field of waste treatment, pyrolysis and gasification and concerns an apparatus for syngas bio-methanation. The invention also concerns a method for syngas bio-methanation, and aims at providing methane from organic material with a low methane potential.

BACKGROUND

Methanation consists in the reaction of hydrogen, carbon monoxide and carbon dioxide to generate methane and water and/or carbon dioxide. Various methanation processes are currently being developed, including catalytic conversion or biological methanation (biocatalysis from microorganisms).

Chemical catalysis processes are expensive and usually require high pressures and temperatures. These disadvantages can be avoided by using the biological pathway to convert the syngas compounds to methane at normal temperatures and pressures. Several studies show that microorganisms are able to convert carbon monoxide (CO) to methane ($CH_4$) under anaerobic conditions.

Anaerobic digestion produces biogas as a result of the biological fermentation of organic solids supplied with the feedstock. Digesters treating complex organic substrates achieve generally between 30 and 60% of solids reduction. The digestate may be dewatered to produce a cake with typically 20 to 30% solids.

But some solids supplied with the feedstock may have a low methane potential. This is the case for example of lignin-rich solids. Such organic feedstock have a low biochemical methane potential. Additionally, the organic feedstock may be too dry (>30% of suspended solids) to be digested in an anaerobic digester. In such cases, pyrolysis may be used.

Pyrolysis is a thermochemical decomposition of organic material at elevated temperatures in absence of oxygen. The organic material can be solid or liquid material. In general, pyrolysis of organic substances produces gas and liquid products and leaves a solid residue rich in carbon content called biochar. High temperature pyrolysis is known as gasification and produces primarily synthesis gas.

Synthesis gas, also called syngas, is a gas comprising CO, $H_2$, $CO_2$ and a small amount of $CH_4$ that results from the thermal degradation of biomass without combustion, through pyrolysis or gasification.

Moreover, the organic feedstock may contain inhibitors to anaerobic digestion or regulated compounds like micropollutants, PAHs, PCBs, aromatic cycles, etc.). These organic compounds may have a low degradation kinetic leading to a long residence time. Consequently, the digester may have an important volume and have a high footprint.

Moreover if syngas was to be injected in an infinitely mixed digester (also called continuous stirred tank reactor), its mass transfer in the liquid may be limited requiring a gaseous recirculation of the gaseous phase, which adds further complexity into the whole process. Furthermore in a digester treating an organic feedstock, the bacterial population used may not be specific to the conversion of syngas.

Finally, during maintenance or shutdown of the digester, the whole system lacks flexibility since it is impossible to biologically convert the syngas in methane. It results in a reduction of the guarantee of the annual production of bio-CH4 and there is a risk of non-valuation of the produced syngas.

SUMMARY OF THE INVENTION

The invention aims to provide a solution to increase the methane content of biogas in a digester while increasing the conversion of organic feedstock, even with a low methanogenic potential by coupling biomethanation of the syngas from the pyrolysis/gasification of this organic feedstock.

To this end, the subject of the invention is an apparatus for syngas bio-methanation comprising a unit for pyrolysis/gasification configured for receiving organic material from an organic deposit and being configured for generating syngas and a membrane bioreactor configured to be placed inside a liquid bath comprising at least one suitable bacteria population, said membrane reactor comprising at least one hollow fiber arranged in such a way that, when the membrane reactor is in contact with the liquid bath, a biofilm is formed around the at least one hollow fiber and so that the syngas generated at the unit for pyrolysis/gasification flows into the at least one hollow fiber so as to convert the syngas into methane.

According to the invention, a suitable population of bacteria is homoacetogenic bacteria and/or acetogenic methanogens or hydrogenotrophic methanogens and/or carboxydotrophic acetogens and acetogenic methanogens. In a preferred embodiment of the invention, a suitable population of bacteria is homoacetogenic bacteria coupled to acetogenic methanogens and hydrogenotrophic methanogens and carboxydotrophic acetogens coupled to acetogenic methanogens.

The apparatus for syngas bio-methanation further comprises an anaerobic digester configured to be fed with organic material, the digester being connected to the outlet of the membrane reactor, so as to inject a gaseous phase with methane and potentially without carbon dioxide into the digester. This increases the content of methane in the digester, resulting in an increase of the lower calorific value of the biogas. Pyrolysing a low methanogenic feedstock and then converting the syngas to methane biologically increases the conversion yield of the organic feedstock (compared to anaerobic digestion alone).

Additionally, for substrate that would implicate low conversion kinetics, the combination of pyrolysis and bio-methanation allows to reduce the residence time compared to what it would be in a digester and consequently reduce the digester size/footprint.

According to another embodiment, the apparatus according to the invention may comprise a dewatering unit configured to dewater the residue from the anaerobic digester, leading to a solid cake and a liquid centrate.

According to another embodiment, the apparatus according to the invention may be configured to inject the centrate from the dewatering of the digestate into the liquid bath of the membrane reactor, so as to provide nutrients to the liquid bath of the membrane reactor, in order to help maintaining the formation of the biofilm on the membrane.

According to another embodiment, the apparatus according to the invention may be configured to feed the cake as an organic material to a unit for pyrolysis/gasification to form syngas gas which is fed back to the anaerobic digester and/or to the membrane. This configuration has the advantage of increasing the part of biogas inside the digester 21 and reducing the cake 24 volume/mass.

According to another embodiment, the apparatus according to the invention may be configured to operate in a closed loop by feeding the cake 24 as the organic material to the unit for pyrolysis/gasification or both the unit for pyrolysis/gasification, and/or by sending the biochar to the organic deposit as potential stabilizing material.

According to another embodiment, the apparatus according to the invention may be configured to add a liquid portion of the outlet stream from the liquid bath of the membrane reactor 16 to the organic material feeding the anaerobic digester. This enables to clean the liquid bath by eliminating the liquid that contains too many bacteria or other particles and cleanse the membrane.

According to another embodiment, the apparatus according to the invention may comprise a plurality of membrane reactors in derivation in relation to each others, thus increasing the flow rate of syngas that can be converted. This configuration also enables to facilitate the renewal of membrane reactors without interrupting the methanation process.

The invention also concerns a method for bio-methanation of syngas comprising a step of providing syngas from a unit for pyrolysis/gasification to a membrane reactor inside a liquid bath comprising at least one suitable bacteria population, said membrane reactor comprising at least one hollow fiber in contact with the liquid bath, around which a biofilm is formed and into which the output syngas of the unit for pyrolysis flows, so as to convert the syngas into methane.

The method for syngas bio-methanation further comprises a step of feeding an anaerobic digester fed with organic material, with the outlet stream of the membrane reactor. This increases the content of methane in the digester, resulting in an increase of the lower calorific value of the biogas produced in the digester.

Advantageously, the method according to the invention further comprises a step of feeding the digestate from the anaerobic digester into a dewatering unit, so as to obtain a solid part, a so-called cake, and a liquid part, a so-called centrate.

Advantageously, the method according to the invention further comprises a step of feeding the centrate from the dewatering unit into the liquid bath of the membrane reactor. This step enables to maintain the biofilm on the hollow fiber(s) for the conversion of syngas into methane.

BRIEF DESCRIPTION OF THE DRAWINGS

The accompanying drawings illustrate various non-limiting, exemplary, innovative aspects in accordance with the present description.

For the sake of clarity, the same elements have the same references in the various figures.

DETAILED DESCRIPTION

Figure 1:
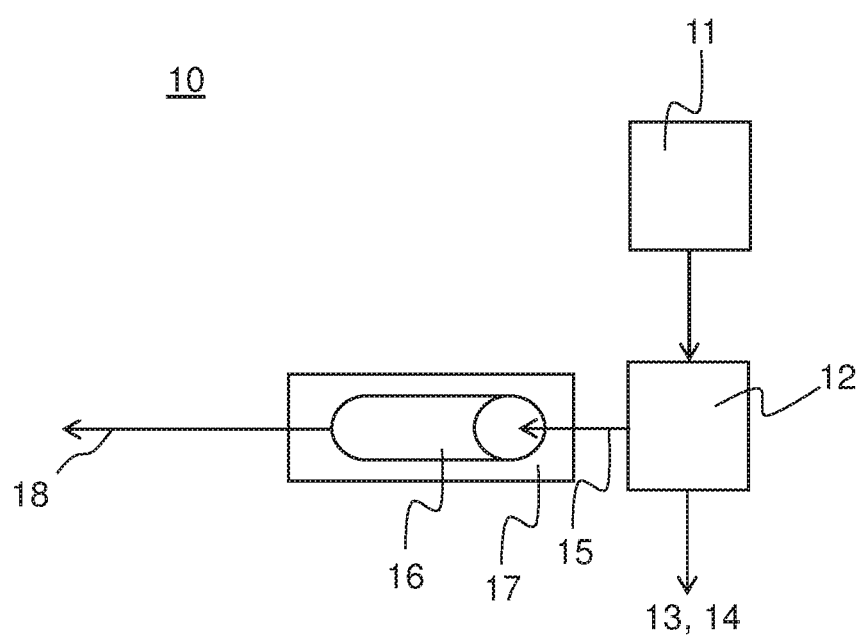
FIG. 1 schematically represents a first embodiment of the apparatus for syngas bio-methanation according to the invention.

FIG. 1 schematically represents a first embodiment of the apparatus 10 for syngas bio-methanation according to the invention. The apparatus 10 comprises a unit 12 for pyrolysis/gasification receiving organic material from an organic deposit 11. The apparatus according to the invention may comprise a drying unit located between the organic deposit 11 and the unit 12 for pyrolysis/gasification to dry the organic feedstock, especially if it has a low dry solid content. The organic material of the organic deposit 11 is preferably solid, but can be liquid. It can be a material rich in carbon. After pyrolysis/gasification, the output of the unit 12 is a combination 15 of CO, $H_2$, $CO_2$ and $CH_4$ on the one hand and ash 13 and biochar 14 and pyrolysis oil on the other hand. The biochar 14 may be used as a soil enhancer.

The apparatus 10 comprises a membrane bioreactor 16 inside a temperature-controlled liquid bath 17. The membrane bioreactor 16 consists of a cartridge where at least one and preferably a plurality of hollow fibers are bundled and potted within a housing. The number of hollow fibers may vary according to the size of the housing and the gaseous flow through the membrane bioreactor 16. It can be between several hundred until few thousand. The hollow fibers are made in a material which is resistant to temperature and allows a good diffusibility to CO and $CO_2$. The fibers constitute a microporous membrane or non-porous membrane or membrane having similar properties that transfer (dissolve) gases into liquids for delivering the components in the syngas directly to the cells that use the CO and H2 in the gas and transform them into methane and other soluble products. The membranes concurrently serve as the support upon which the fermenting cells grow as a biofilm and are thus retained in a concentrated layer. The result is a highly efficient and economical transfer of the syngas at essentially 100% dissolution and utilization, overcoming limitations for the other fermentation methods and fermenter configurations. For example, the hollow fibers can be in polyvinylidenedifluoride.

The membrane reactor 16 is located downstream the unit 12 for pyrolysis/gasification and is fed with the syngas from the unit 12.

Ideally operated at 35° C. but is also possible at 42° C. and 55° C. The higher the temperature, the more limiting the transfer of mass from the gas phase to the liquid phase and also, the more the membranes aging is accelerated. Also, the increase of the temperature is a problem in case of high ammonium concentration because there is then ammonia in the gaseous phase (since the pKa of NH4+/NH3 decreases with the temperature increase).

Concerning the syngas pressure, it is normally not expected to inject syngas into the membranes at a pressure greater than 2.5 bar. The apparatus according to the invention may comprise a compressor between the unit 12 for pyrolysis/gasification and the membrane reactor(s) depending on the installation. Furthermore, the apparatus according to the invention may comprise a condenser and/or purge pot to cool the syngas and drain water into the syngas between the unit 12 for pyrolysis/gasification and the membrane reactor(s).

Such a membrane reactor constitutes a bio-support membrane suitable for permeation of at least one of CO, $CO_2$, $H_2$ and provides the separation between the feed gas 15 and a liquid phase constituted by the liquid bath 17.

Figure 2A:
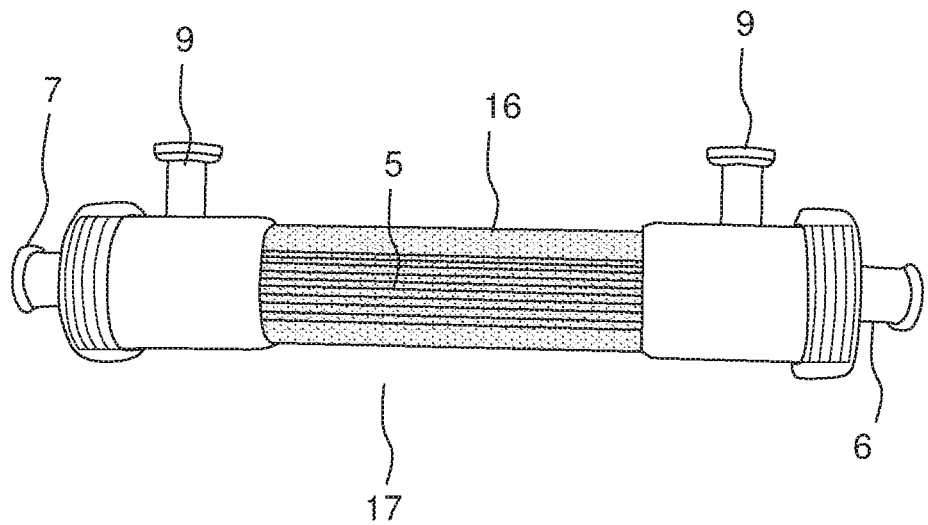
FIGS. 2A-2B schematically represent an embodiment of the membrane reactor of the apparatus for syngas bio-methanation according to the invention.
Figure 2B:
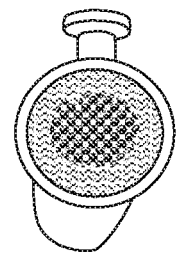

FIGS. 2A-2B schematically represent an embodiment of the membrane reactor of the apparatus for syngas bio-methanation according to the invention. The part on the left hand side (part A) represents a side view of the membrane reactor 16. The reactor 16 comprises two lateral inlet/outlet ports 9 for fluid feeding/outlet from the liquid bath 17. The stream 15 enters the membrane reactor by the inlet port 6 and flows into the hollow fibers 5. Each hollow fiber has a nominal pore size, an inner and outer diameter and a useful length, as well as an outer surface area. The part on the right hand side (part B) represents a cut section of the membrane reactor 16. The feeding gas (i. e. syngas) is supplied at one end of the cartridge and conveyed inside the fibers to diffuse through the membrane, without gas recirculation. The lateral inlet/outlet ports 9 are fed with the liquid bath 17 as inlet/outlet of the liquid, which is a defined media solution for a predetermined average hydraulic retention time. Liquid can flow against or parallel to the gas flow. The pH of the liquid bath as well as the liquid pressure may be monitored and controlled by using corresponding devices. The fiber membrane serves as a support for the microbial population as well as an interface between the gas and the liquid phases.

The liquid bath can be water, either treated water or partially treated water, which contains various populations of bacteria. When operating, a biofilm develops on the membrane made of fibers, depending on the inlet stream in the membrane reactor. In other words, only population of bacteria in adequacy with the substrate in the reactor can grow. The culture of bacteria fixes on the membrane. These populations of bacteria enable to conversion of the stream 15 into $CH_4$ essentially and a part of $CO_2$ and $H_2O$. As suitable populations of bacteria, it can be cited carboxydotrophic acetogens and acetogenic methanogens according to following chemical elementary reactions:

$$4CO + 2H_2O \rightarrow CH_3COOH + 2CO_2$$

$$CH_3COOH \rightarrow CH_4 + CO_2$$

This leads to the global reaction: 4 $CO + 2\ H_2O = CH_4 + 3\ CO_2$.

Another suitable population of bacteria is homoacetogenic bacteria and acetogenic methanogens or hydrogenotrophic methanogens leading to following chemical elementary reactions:

$$4H_2 + 2CO_2 \rightarrow CH_3COOH + 2H_2O$$

$$CH_3COOH \rightarrow CH_4 + CO_2$$

$$4H_2 + CO_2 \rightarrow CH_4 + 2H_2O$$

This leads to the global reaction: 4 $H_2 + CO_2 = CH_4 + 2\ H_2O$.

When combining these reactions, it leads to $CO + 3H_2 = CH_4 + H_2O$.

Thanks to the biofilm formed in the membrane reactor 16, the carbon monoxide and carbon dioxide contained in the stream 15 are converted into $CH_4$. This stream containing mainly $CH_4$ can be extracted from the liquid bath 17 and is schematically represented in FIG. 1 by the reference 18. The apparatus according to the invention may therefore comprise a phase separator (not represented) to separate the gaseous from the liquid phase.

It can be noted that the disposal of the hollow fibers 5 inside the membrane reactor 16 may be different. The idea is to have an increasing number of modules containing the fibers as a function of the flow of syngas to be processed. The disposal of the hollow fibers should enable a flexibility in their implementation and operation for maintenance, without causing too much pressure drop. As another example, the membrane reactor may comprise a central longitudinal fiber receiving the input syngas and feeding, at regular spatial intervals or not, series of fibers extending perpendicularly to the central fiber. The advantage is then that it is possible to maintain a certain degree of conversion of the syngas to methane even if one is limited in length of reactor, precisely by playing on the exchange surface perpendicular to the central axis.

As the liquid bath 17 should contain suitable bacteria, it can be fed by an annex culture medium of bacteria.

The combination of the membrane reactor 16 and the unit 12 for pyrolysis/gasification therefore leads to a better conversion of organic material into methane. Thanks to the membrane reactor, the conversion rate of syngas into methane is about 80-90%.

Figure 3:
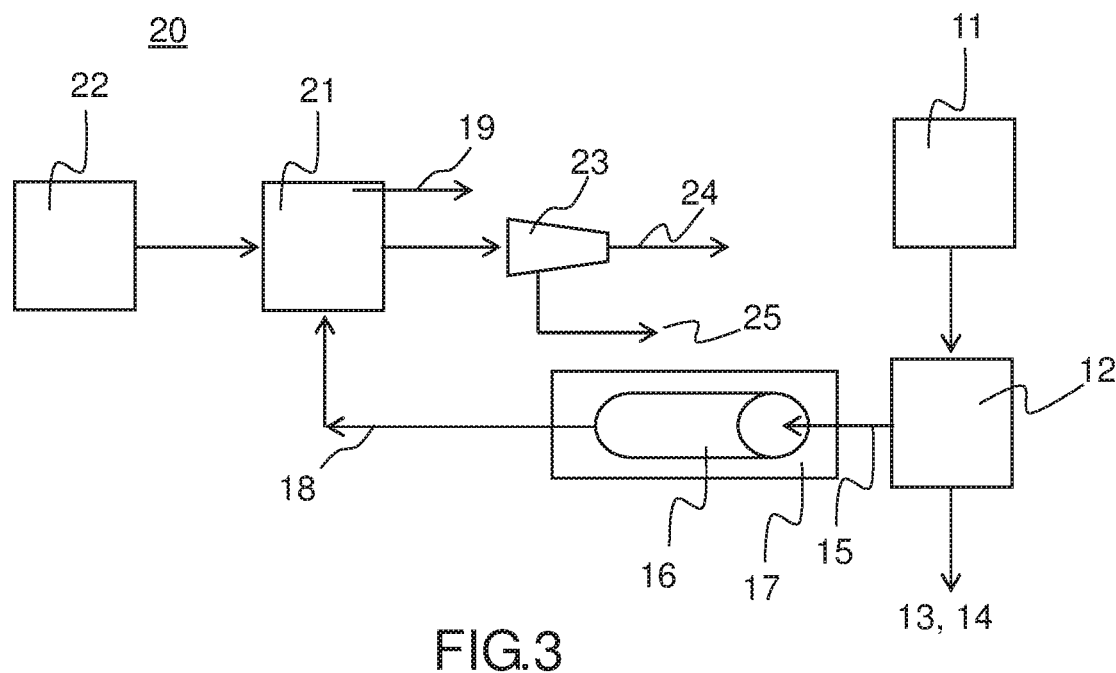
FIG. 3 schematically represents another embodiment of the apparatus for syngas bio-methanation according to the invention.

FIG. 3 schematically represents another embodiment of the apparatus 20 for syngas bio-methanation according to the invention. The apparatus 20 comprises the same elements as the apparatus 10 presented in FIG. 1. Additionally, the apparatus 20 comprises an anaerobic digester 21 fed by an organic deposit 22 containing organic material which can be solid, liquid. As explained before, anaerobic digestion produces biogas as a result of the biological fermentation of organic material. This biogas contains among others $CH_4$. Methane can be extracted at this stage from the biogas (reference 19). The rate of methan in the biogas may vary between 55 and 75%.

In another embodiment of the invention, there can be a plurality of digesters 21, each of the digesters 21 can be fed with one or more organic deposit and/or with the output stream of the membrane reactor.

The apparatus 20 may comprise a dewatering unit 23 configured to dewater the residue from the anaerobic digester 21. The dewatering leads to a cake 24 and a liquid centrate 25. Furthermore, the pyrolysis oil can be either sent to the digester, or discarded. It is not advised to send it to the membrane due to risks of fouling and inhibition of the population.

Figure 4:
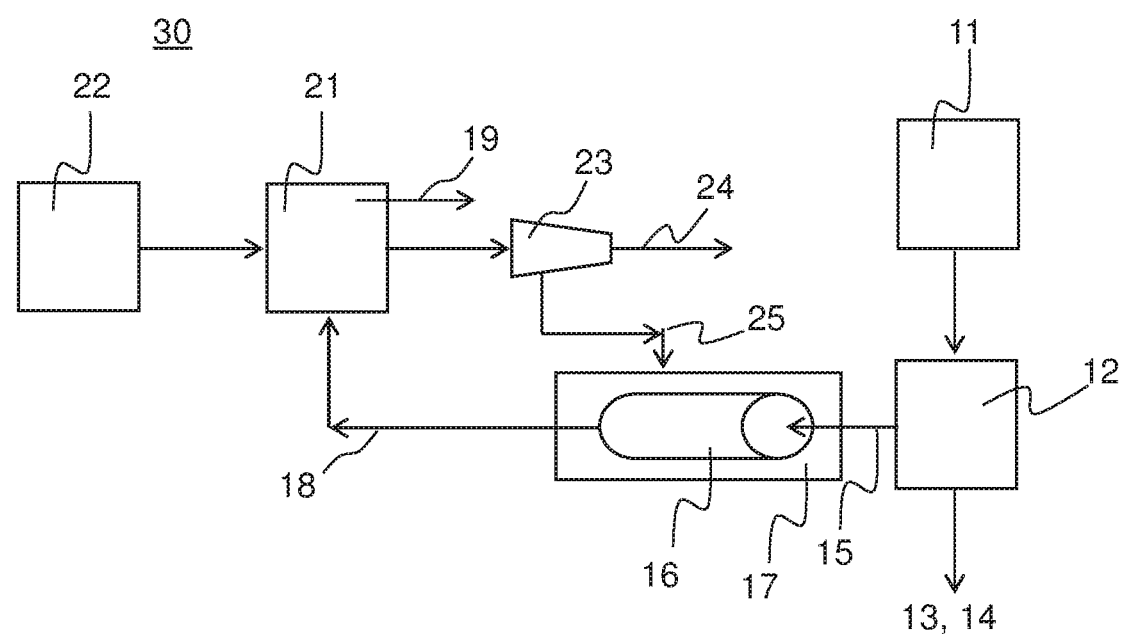
FIG. 4 schematically represents another embodiment of the apparatus for syngas bio-methanation according to the invention.

FIG. 4 schematically represents another embodiment of the apparatus 30 for syngas bio-methanation according to the invention. The apparatus 30 comprises the same elements as the apparatus 20 presented in FIG. 3. In the embodiment of FIG. 4, the centrate 25 is sent into the liquid bath 17. The centrate 25 constitutes a culture medium to provide nutrient support and bacteria to the liquid bath 17 of the membrane reactor 16, so as to help the formation of the biofilm on the membrane.

Figure 5:
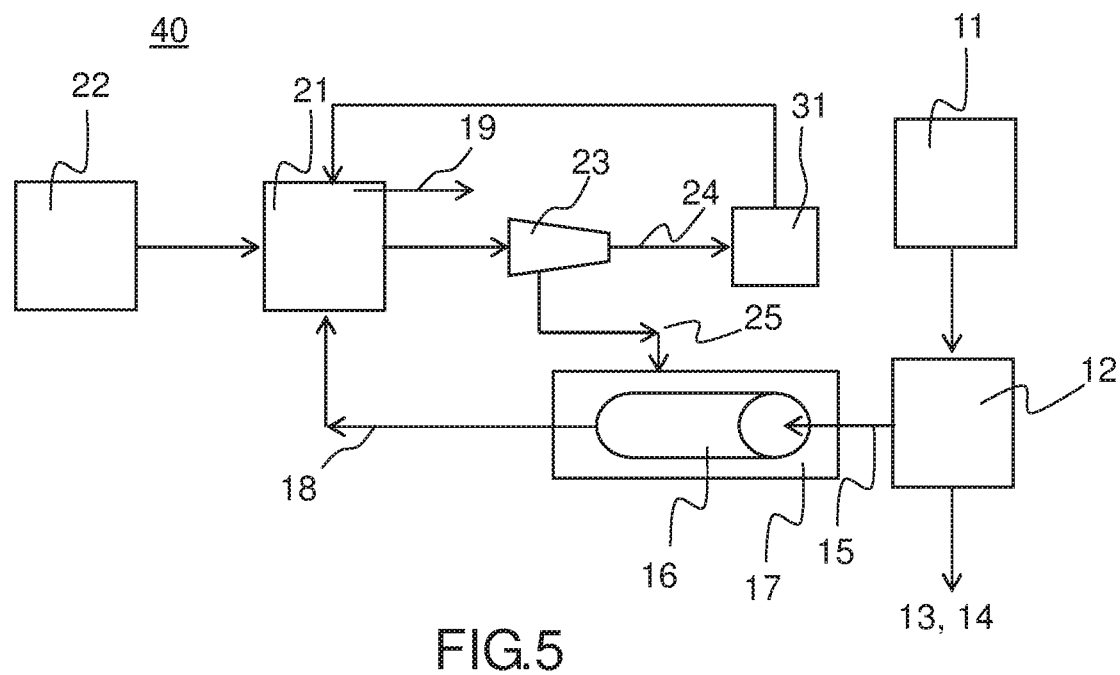
FIG. 5 schematically represents another embodiment of the apparatus for syngas bio-methanation according to the invention.

FIG. 5 schematically represents another embodiment of the apparatus 40 for syngas bio-methanation according to the invention. The apparatus 40 comprises the same elements as the apparatus 30 presented in FIG. 4. In the embodiment of FIG. 5, the cake 24 is fed as an organic material to a dedicated unit for pyrolysis/gasification 31 to form syngas or both the unit 31 and the digester 21. This configuration has the advantage of increasing the part of biogas inside the digester 21 and minimizing the cake volume.

It can be noted that the unit for pyrolysis/gasification 31 is not compulsory. As an alternative, the cake 24 can also be fed to the unit 12 for pyrolysis/gasification or both the unit 12 and the digester 21, I the unit 12 is suitable to work from two flows of different organic deposits.

Figure 6:
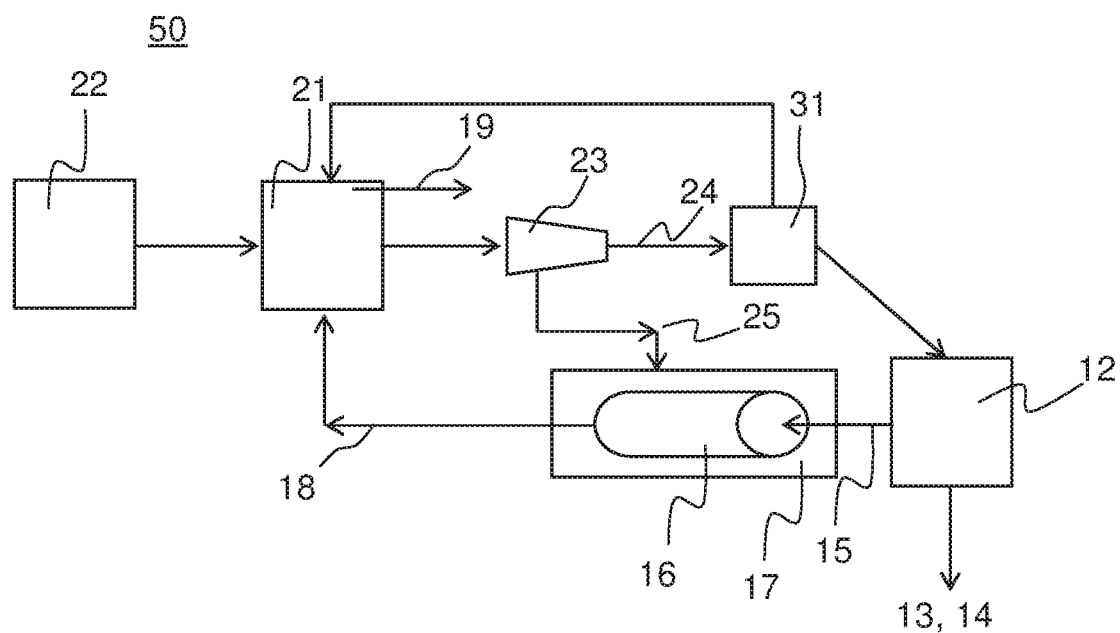
FIG. 6 schematically represents another embodiment of the apparatus for syngas bio-methanation according to the invention.

FIG. 6 schematically represents another embodiment of the apparatus 50 for syngas bio-methanation according to the invention. The apparatus 50 comprises the same elements as the apparatus 40 presented in FIG. 5, except the organic deposit 11. In the embodiment of FIG. 6, the cake 24 is the organic material that feeds either only the unit 12 for pyrolysis/gasification or both the unit 12 for pyrolysis/gasification and the unit 31. This configuration enables to operate in a closed loop. Methane 19 can be obtained from the digester 21. Centrates from the anaerobic digester 21 are sent to the membrane reactor 16 for the liquid part to participate to the formation of the biofilm on the membrane and to the unit 12 for pyrolysis/gasification for the solid part to produce syngas. Actually, only a small part of the centrate are sent to the membrane reactor. Th rest part goes to headworks or sidestream treatment.

Figure 7:
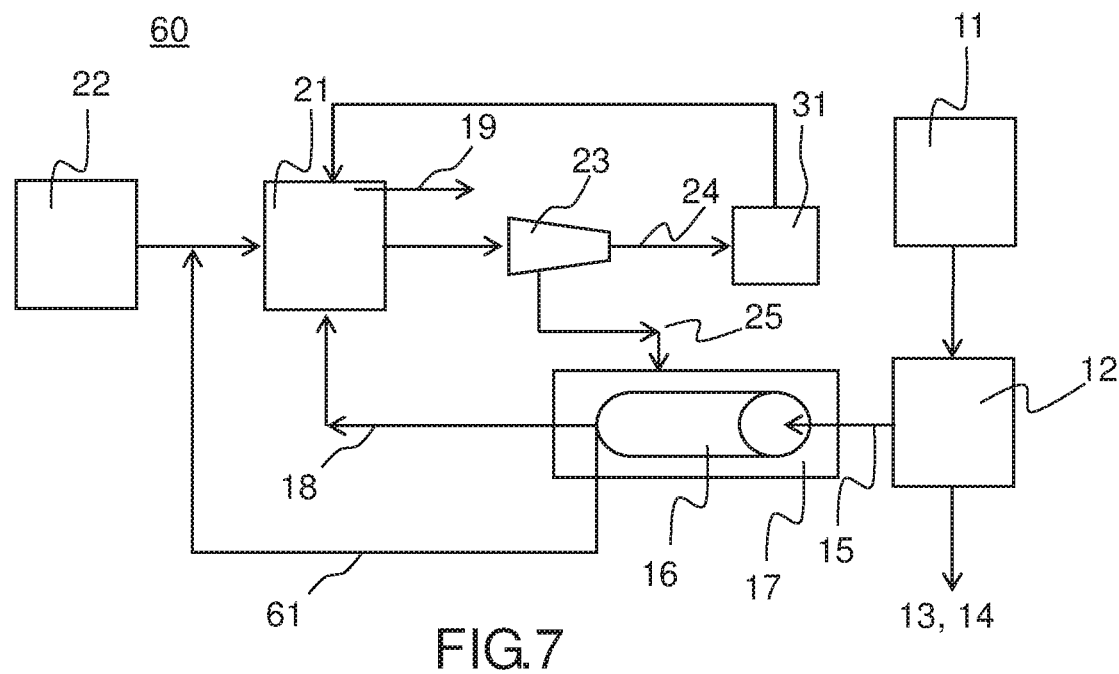
FIG. 7 schematically represents another embodiment of the apparatus for syngas bio-methanation according to the invention.

FIG. 7 schematically represents another embodiment of the apparatus 60 for syngas bio-methanation according to the invention. The apparatus 60 comprises the same elements as the apparatus 20, 30, 40 or 50 presented in the previous figures. In the embodiment of FIG. 7, a liquid portion 61 of the outlet stream from the liquid bath 17 of the membrane reactor 16 is added to the organic material feeding the anaerobic digester 21. This enables to clean the liquid bath by eliminating the liquid that contains too many bacteria or other particles or fermentation by-product (such as volatile fatty acids). Adapting the recirculation velocity of this stream is a way to cleanse the membrane. If the recirculation velocity is increased, the biofilm might be partially or totally scoured.

Figure 8:
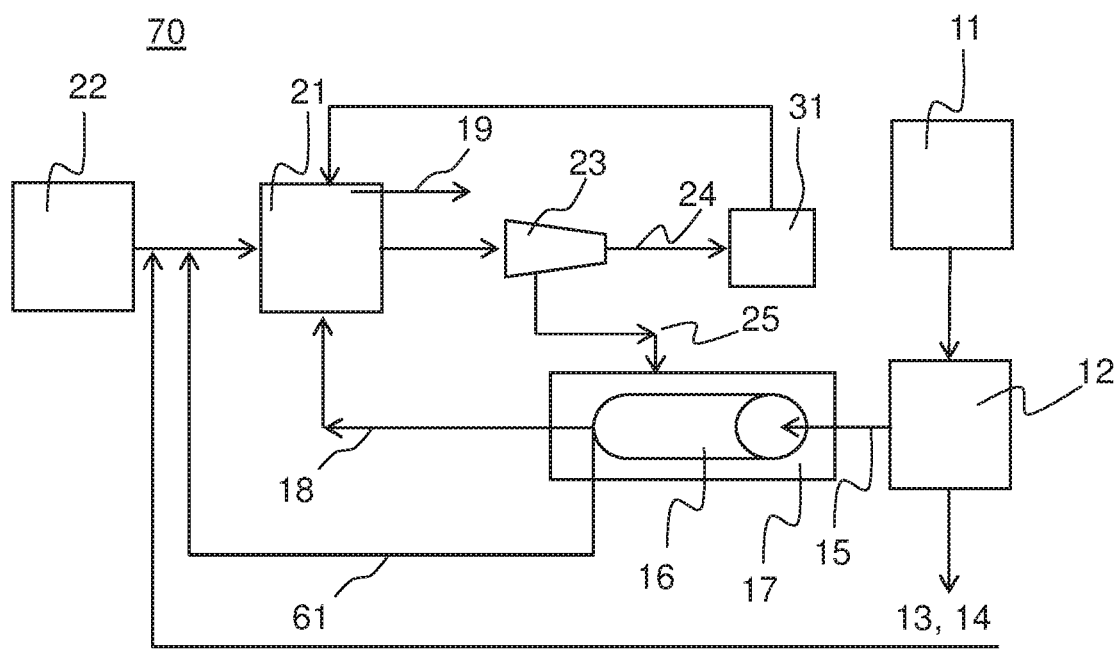
FIG. 8 schematically represents another embodiment of the apparatus for syngas bio-methanation according to the invention.

FIG. 8 schematically represents another embodiment of the apparatus 70 for syngas bio-methanation according to the invention. The apparatus 70 comprises the same elements as the apparatus 20, 30, 40, 50 or 60 presented in the previous figures. In the embodiment of FIG. 8, the biochar 14 is sent directly to feed the anaerobic digester 21. This configuration enables to operate in a closed loop, since the residue from the pyrolysis at the unit 12 is used as a potential stabilisation material for the anaerobic digester 21.

Figure 9:
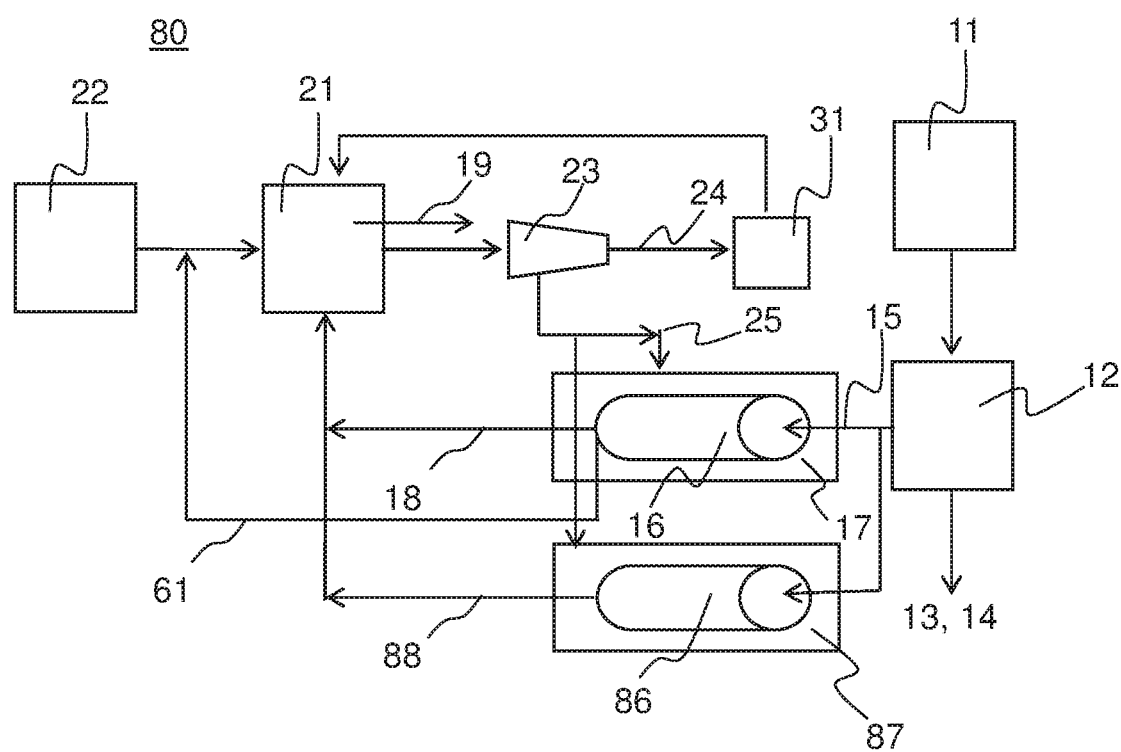
FIG. 9 schematically represents another embodiment of the apparatus for syngas bio-methanation according to the invention.

FIG. 9 schematically represents another embodiment of the apparatus 80 for syngas bio-methanation according to the invention. The apparatus 80 comprises the same elements as the apparatus 10, 20, 30, 40, 50, 60 or 70 presented in the previous figures. In the embodiment of FIG. 9, the apparatus 80 comprises two membrane reactors 16 and 86. The additional membrane reactor 86 is inside a liquid bath 87. It can be the same type of liquid bath as discussed previously for the liquid bath 17, or it can be water with another type of medium culture suitable for the conversion of the stream 15 into methane. Nevertheless, with a syngas from the same unit 12 for pyrolysis/gasification, there is no justification for changing the media where the biomass is growing, so in this case, it should be the same liquid bath.

The membrane reactor 86 is located downstream the unit 12 for pyrolysis/gasification and is fed with the syngas from the unit 12. The membrane reactor 86 is positioned in derivation compared to the membrane reactor 16, that is to say that the stream 15 may be split into two streams, the first one feeding the membrane reactor 16, the second one feeding the membrane reactor 86. The configuration with two membrane reactors increases the flow rate of syngas that can be converted. And for a predetermined flow rate of syngas to convert, the configuration with two membrane reactors avoids the need of a huge membrane with too many fibers that would make the installation of such a huge membrane cumbersome.

It can be noted that the embodiment with two membrane reactors represented in FIG. 9 is only represented so to illustrate the possibility of two membrane reactors. According to the invention, the embodiment can also be a combination of a first membrane 16 and a second membrane 86 both as described in FIG. 1 or a first membrane reactor 16 as described in figure land a second membrane reactor 86 as described in FIGS. 2A-2B, 3, 4, 5, 6, 7 or 8, or both membrane reactors 16, 86 as described in FIGS. 2A-2B, 3, 4, 5, 6, 7, or 8. All the possible combinations of the embodiments presented in the previous figures are within the framework of the invention.

Figure 10:
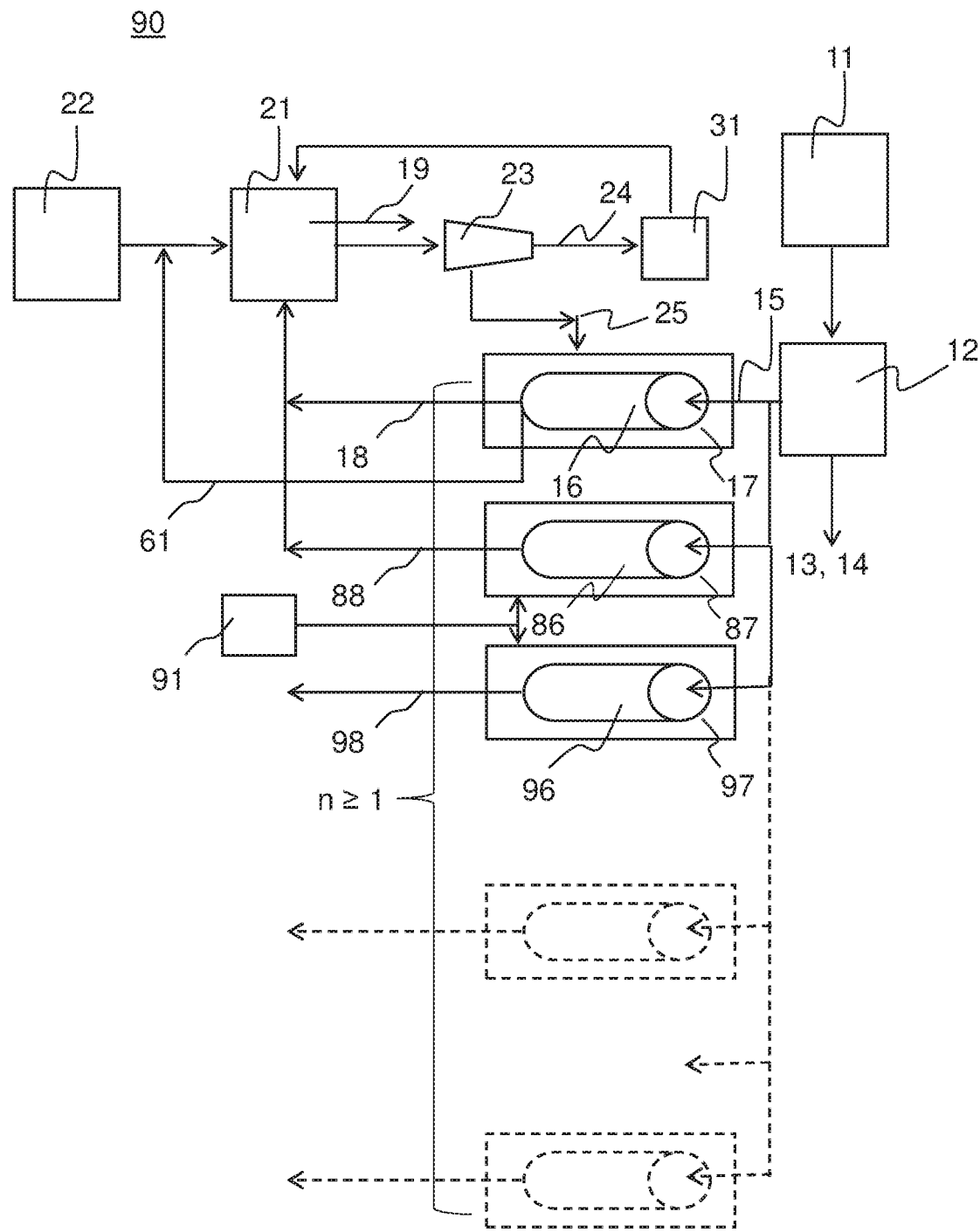
FIG. 10 schematically represents another embodiment of the apparatus for syngas bio-methanation according to the invention.

FIG. 10 schematically represents another embodiment of the apparatus 90 for syngas bio-methanation according to the invention. The apparatus 90 comprises the same elements as the apparatus 10, 20, 30, 40, 50, 60, 70 or 80 presented in the previous figures. In the embodiment of FIG. 10, the apparatus 90 comprises three membrane reactors 16, 86, 96. The additional membrane reactor 96 is inside a liquid bath 97. It can be the same type of liquid bath as discussed previously for the liquid bath 87, or it can be water with another type of medium culture suitable for the conversion of the stream 15 into methane. Nevertheless, with a syngas from the same unit 12 for pyrolysis/gasification, there is no justification for changing the media where the biomass is growing, so in this case, it should be the same liquid bath.

The membrane reactor 96 is located downstream the unit 12 for pyrolysis/gasification and is fed with the syngas from the unit 12. The membrane reactor 96 is positioned in derivation compared to the membrane reactor 16 and the membrane reactor 86. The embodiment presented in FIG. 10 is an illustration for one of the various possible combinations for the apparatus according to the invention. In this embodiment, the liquid bath 17 is fed with the centrate 25 whereas the liquid bathes 87 and 97 are fed with an annex culture medium 91. The gaseous part (mainly methane) 18 of the output stream of the membrane reactor 16 is fed into the anaerobic digester 21 and the rest part of the output stream of the membrane reactor 16 is fed into the organic material feeding the anaerobic digester 21. The whole part of the output stream 88 of the membrane reactor 86 is injected into the anaerobic digester 21 whereas the whole part of the output stream 98 of the membrane reactor 96 is not injected into the apparatus.

In the previous explanation, the output stream of the membrane reactor 16 is considered with a gaseous part of methane and the rest as a liquid part. This is for the sake of explanation. In fact, the output stream of the membrane reactor should be seen as a gaseous pocket in the liquid bath and this gaseous pocket together with some liquid of the liquid bath is sampled from the liquid bath and injected into the anaerobic digester. The removal of this part of the liquid bath is compensated by the addition of the centrate and both ensure the durability of the biofilm as well as the scouring and cleaning of the biofilm by adapting the recirculation velocity of the liquid when the membrane is saturated.

Of course, the scope of the invention also concerns an apparatus with more than 2 or 3 membrane reactors, for example 5, 10, 20, etc.

Figure 11:
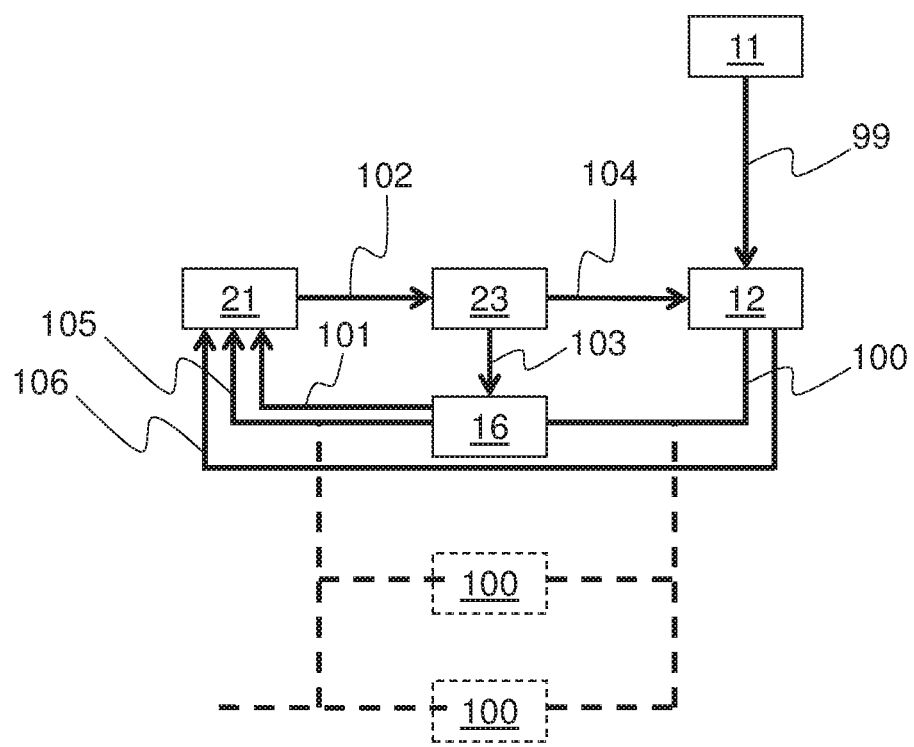
FIG. 11 schematically represents a block diagram with the step(s) of a method for syngas bio-methanation according to the invention.

FIG. 11 schematically represents a block diagram with the step(s) of a method for bio-methanation of syngas according to the invention. The method according to the invention comprises a step 100 of providing syngas from a unit for pyrolysis/gasification to a membrane reactor inside a liquid bath comprising at least one suitable bacteria population, said membrane reactor comprising at least one hollow fiber in contact with the liquid bath, around which a biofilm is formed and into which the output syngas of the unit for pyrolysis flows, so as to convert the syngas into methane.

Before step 100, the method may comprise a step 99 of providing organic material into a unit of pyrolysis/gasification to form syngas.

In a preferred embodiment of the invention, the method for syngas bio-methanation further comprises a step 101 of feeding an anaerobic digester fed with organic material, with the outlet stream of the membrane reactor. This increases the content of methane in the digester, resulting in an increase of the lower calorific value of the biogas produced in the digester.

Advantageously, the method according to the invention further comprises a step 102 of feeding the digestate from the anaerobic digester into a dewatering unit, so as to obtain a solid part, a so-called cake, and a liquid part, a so-called centrate.

Advantageously, the method according to the invention further comprises a step 103 of feeding the centrate from the dewatering unit into the liquid bath of the membrane reactor. This step enables to feed the liquid bath of the membrane reactor with at least one suitable bacteria population to form the biofilm on the hollow fiber(s) for the conversion of syngas into methane.

Advantageously, the method according to the invention further comprises a step 104 of feeding the cake from the dewatering unit into the unit for pyrolysis/gasification (either unit 12 or another unit for pyrolysis/gasification). This step enables to form syngas gas from a residue of the digester which is fed back to the anaerobic digester 21. This results in an increase of the part of biogas inside the digester 21 while suppressing any solid residue. When comprising the step 104, the method according to the invention may not comprise the step 99 of providing organic material into a unit of pyrolysis/gasification to form syngas, since the organic material is the cake from the dewatering unit.

According to another embodiment, the method according to the invention may comprise a step 105 of adding a liquid portion of the outlet stream from the liquid bath of the membrane reactor to the organic material feeding the anaerobic digester. This enables to clean the liquid bath by eliminating the liquid that contains too many bacteria or other particles.

According to another embodiment, the method according to the invention may comprise a step 106 of sending the biochar to the organic deposit as a potential stabilisation material or it can be directly fed into the anaerobic digester. This configuration enables to operate in a closed loop, since the residue from the pyrolysis at the unit is used as a potential stabilisation material for the anaerobic digester.

According to another preferred embodiment, the method according to the invention may comprise a plurality of step 100, meaning that the apparatus according to the invention comprises a plurality of membrane reactors. In FIG. 11, 3 steps 100 are illustrated. It is not limited to 3, there can be more steps 100, depending on the number of the membrane reactors, as explained before. In other words, if there are 10 membrane reactors, there can be 10 steps 100 of providing syngas to the reactor. Moreover, it is also possible to have 10 membrane reactors but only 1, 2, 3 . . . or 9 steps 100, if it is desired not to use all the membrane reactors, depending on the flow rate of syngas to treat. Similarly, with one membrane reactor, there can be a plurality of digesters 21, resulting in more than one step 101 of feeding an anaerobic digester with the output stream of the membrane reactor.

The examples disclosed in this specification are only illustrative of some embodiments of the invention. They do not in any way limit the scope of said invention and all possible combinations of the presented embodiments are within the framework of the invention.

The invention claimed is:

1. An apparatus for syngas bio-methanation comprising:
   a unit for pyrolysis/gasification configured to receive organic material, the unit for pyrolysis/gasification being configured to generate syngas;
   at least one membrane reactor configured to be placed inside a liquid bath, the liquid bath comprising at least one bacteria population, the at least one membrane reactor comprises at least one hollow fiber arranged in such a way that, when the membrane reactor is in contact with the liquid bath, a biofilm is formed around the at least one hollow fiber and so that the syngas generated at the unit for pyrolysis/gasification flows into the at least one hollow fiber, so as to convert the syngas into methane; and
   an anaerobic digester configured to be fed with organic material and to generate biogas comprising methane and a digestate,
   wherein an inlet of the digester is connected in series to an outlet of the at least one membrane reactor, and
   wherein the at least one membrane reactor is outside of the digester.

2. The apparatus according to claim 1, further comprising a dewatering unit configured to dewater the digestate from the anaerobic digester so as to lead to a solid cake and a liquid centrate.

3. The apparatus according to claim 2, wherein the apparatus is configured to inject at least a part of the liquid centrate into the liquid bath of the at least one membrane reactor.

4. The apparatus according to claim 2, wherein the apparatus is configured to feed the solid cake to the unit for pyrolysis/gasification or to a second unit for pyrolysis/gasification.

5. The apparatus according to claim 1, wherein the apparatus is configured to add a liquid portion of an outlet stream from the liquid bath of the at least one membrane reactor to the organic material configured to feed the anaerobic digester.

6. The apparatus according to claim 1, further comprising a plurality of membrane reactors, wherein the plurality of membrane reactors are positioned in derivation in relation to each other.

7. The apparatus according to claim 1, wherein the at least one population of bacteria is homoacetogenic bacteria and/or acetogenic methanogens or hydrogenotrophic methanogens and/or carboxydotrophic acetogens and acetogenic methanogens.

8. A method for syngas bio-methanation, comprising:
a step of providing syngas from a unit for pyrolysis/gasification receiving organic material to at least one membrane reactor inside a liquid bath comprising at least one bacteria population, said at least one membrane reactor comprising at least one hollow fiber in contact with the liquid bath, around which a biofilm is formed and into which the syngas from the unit for pyrolysis/gasification flows, so as to convert the syngas into methane, and sequentially, a step of feeding an anaerobic digester at an inlet of the anaerobic digester-with organic material and generating biogas comprising methane and a digestate with an outlet stream of the at least one membrane reactor.

9. The method according to claim 8, further comprising a step of feeding the digestate from the anaerobic digester into a dewatering unit configured to dewater the digestate from the anaerobic digester leading to a solid cake and a liquid centrate.

10. The method according to claim 9, further comprising a step of injecting at least a part of the liquid centrate into the liquid bath of the at least one membrane reactor.

11. The method according to claim 9, further comprising a step of feeding the solid cake to the unit for pyrolysis/gasification or to a second unit for pyrolysis/gasification.

12. The method according to claim 8, further comprising a step of adding a liquid portion of an outlet stream from the liquid bath of the at least one membrane reactor to the organic material feeding the anaerobic digester.

13. The method according to claim 8, wherein the at least one population of bacteria is homoacetogenic bacteria and/or acetogenic methanogens or hydrogenotrophic methanogens and/or carboxydotrophic acetogens and acetogenic methanogens.

14. The method according to claim 8, wherein the at least one membrane reactor is outside of the digester.

* * * * *